United States Patent
Mizutani et al.

[11] Patent Number: 5,795,345
[45] Date of Patent: Aug. 18, 1998

[54] SANITARY NAPKIN

[75] Inventors: Satoshi Mizutani; Kenichi Hisada, both of Ehime-ken, Japan

[73] Assignee: Uni-Charm Corporation, Ehime-ken, Japan

[21] Appl. No.: 731,808

[22] Filed: Oct. 21, 1996

[30] Foreign Application Priority Data

Oct. 19, 1995 [JP] Japan .................................. 7-271253

[51] Int. Cl.⁶ .............................. A61F 13/15; A61F 13/20
[52] U.S. Cl. .............................. 604/380; 604/385.1
[58] Field of Search ..................... 604/358, 380, 604/378, 385.1, 379, 382, 383, 384

[56] References Cited

U.S. PATENT DOCUMENTS

| | | | |
|---|---|---|---|
| 3,897,784 | 8/1975 | Fitzgerald | 604/380 |
| 4,790,838 | 12/1988 | Pigneul et al. | |
| 5,092,860 | 3/1992 | Pigneul | 604/380 |
| 5,387,206 | 2/1995 | Valentine et al. | 604/380 |
| 5,451,442 | 9/1995 | Pieniak et al. | 604/380 |
| 5,578,024 | 11/1996 | Mizutani et al. | 604/385.1 |
| 5,591,150 | 1/1997 | Olsen et al. | 604/380 |
| 5,662,634 | 9/1997 | Yamamoto et al. | 604/380 |

FOREIGN PATENT DOCUMENTS

| | | |
|---|---|---|
| 0 267 059 | 5/1988 | European Pat. Off. |
| 0 291 316 | 5/1988 | European Pat. Off. |
| 3718076 | 12/1987 | Germany. |
| 2 193 100 | 2/1988 | United Kingdom. |
| 93/12747 | 7/1993 | WIPO. |

*Primary Examiner*—John G. Weiss
*Assistant Examiner*—Ki Yong O
*Attorney, Agent, or Firm*—Lowe Hauptman Gopstein Gilman & Berner

[57] ABSTRACT

A sanitary napkin comprising a pair of grooves being formed in a top surface of the napkin by compression-molding along transversely opposite sides of the napkin, and each of these grooves has lower and higher density compressed zones arranged on a bottom thereof alternately in a longitudinal direction thereof.

5 Claims, 2 Drawing Sheets

SANITARY NAPKIN

FIELD OF THE INVENTION

The present invention relates generally to a sanitary napkin and more particularly to a female sanitary napkin or pad to absorb and retain body exudates such as menes.

BACKGROUND OF THE INVENTION

Japanese Utility Model Application Publication No. Hei 5-39691 discloses a sanitary napkin having compression-molded grooves surface thereof. along transversely opposite sides thereof the sanitary napkin includes a pair of longitudinally extending compression-molded grooves spaced from each other by a distance that gradually increases from a minimum distance at longitudinally middle points thereof to a maximum distance at longitudinally opposite ends thereof. Such grooves provide enhanced fit of the napkin against the wearer's body. In addition. the presence of such grooves effectively prevents twisting from occurring in a central region of the napkin thereby forming folds which extend to the transversely opposite side edges of the napkin. In this way. it become possible to avoid a problem that a quantity of body exudates might flow along the fold created by the twist to the side edges of the napkin and cause sideway leakage onto the wearer's undergarments.

However. in a liquid-absorbent core incorporated in the napkin. the compression-molded grooves create areas in the liquid-absorbent core having a density substantially higher than a density in the central region of the napkin. The higher density regions along the grooves rapidly spread a large quantity of body exudates along the length of the grooves. In view of the fact that the grooves are usually formed adjacent the transversely opposite side edges of the liquid-absorbent core. such rapid spreading of body exudates stains the side edges of the napkin. Consequently the wearer's undergarments become stained due to their in contact with the stained side edges of the napkin more often than in a napkin without such grooves.

SUMMARY OF THE INVENTION

Accordingly, it is a principal object of the invention to suppress the spread of body exudates along the grooves formed in sanitary napkin while maintaining an advantageous effect of such grooves.

The object set forth above is achieved. according to the invention. by a sanitary napkin comprising a liquid-permeable topsheet, a liquid-impermeable backsheet and a liquid-absorbent core disposed therebetween. The sanitary napkins includes a pair of grooves formed by compression-molding in a top surface of an absorbing region defined by the core. The grooves extend longitudinally along transversely opposite sides of the absorbing region and the grooves are spaced apart from each other by a distance that gradually increases from a minimum distance at longitudinally middle points thereof to a maximum distance at longitudinally opposite ends thereof. The sanitary napkin is characterized by the fact that each of the grooves has higher and lower density compressed zones alternately arranged in a longitudinal direction thereof.

DETAILED DESCRIPTION OF THE PREFERRED EMBODIMENT

Figure 1:
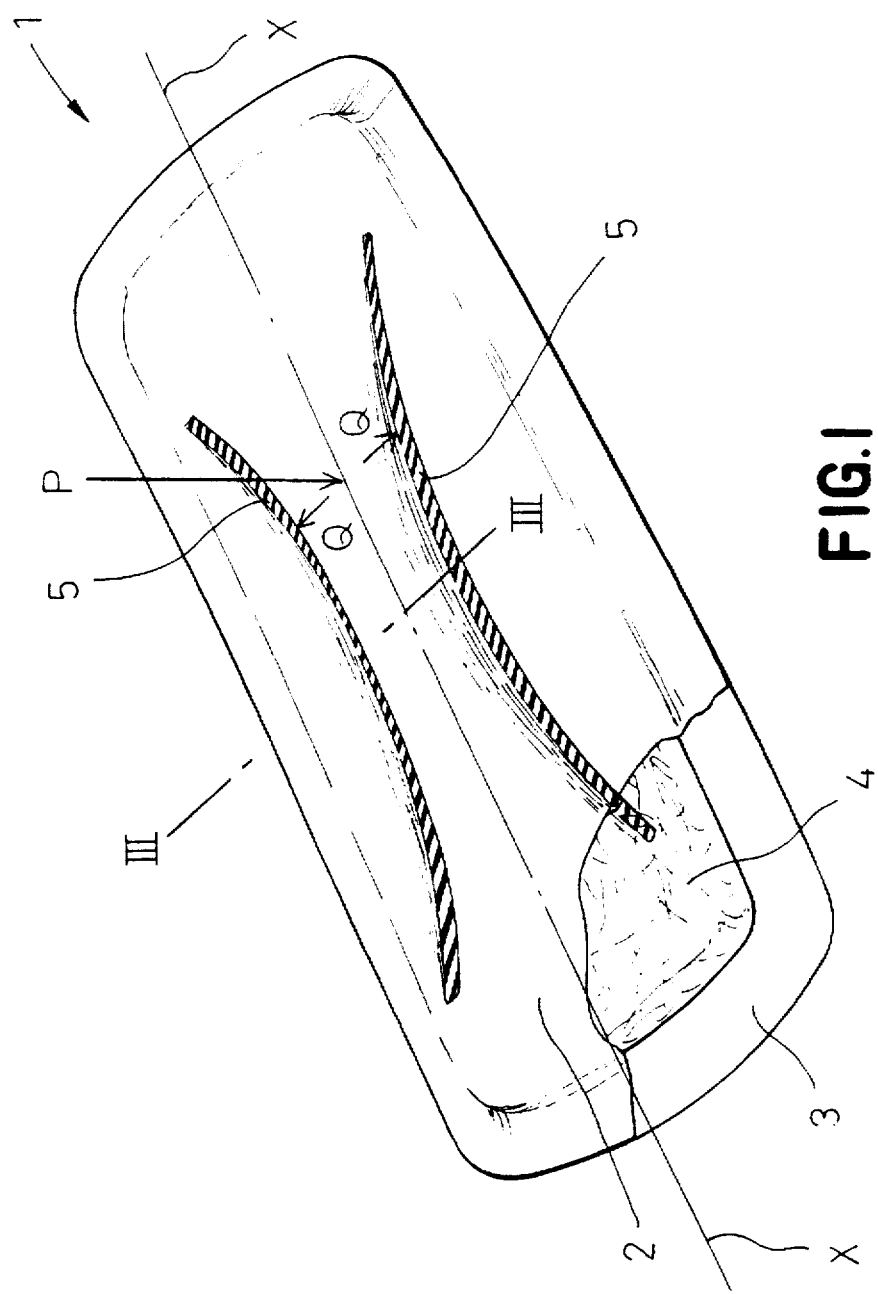
FIG. 1 is a perspective view showing an embodiment of the inventive sanitary napkin as partially broken away.

A sanitary napkin 1 shown by FIG. 1 in a perspective view as partially broken away comprises a liquid-permeable topsheet 2. a liquid-impermeable backsheet 3 and a liquid-absorbent core 4. The topsheet 2 and the backsheet 3 are placed one upon another with inner surfaces opposed to each other and bonded together in a water-tight manner portions extending outward beyond a peripheral edge of the core 4. A pair of compression-molded grooves 5 are formed on an upper surface of the napkin 1 longitudinally extend along transversely opposite sides thereof. At a longitudinally middle region of the napkin 1. the compression-molded grooves 5 are spaced apart from each other by the minimum distance and this distance is progressively enlarged toward longitudinally opposite ends of the napkin 1. The grooves 5 effectively serve to provide enhanced fit of the napkin 1 against the wearer's body.

Figure 2:
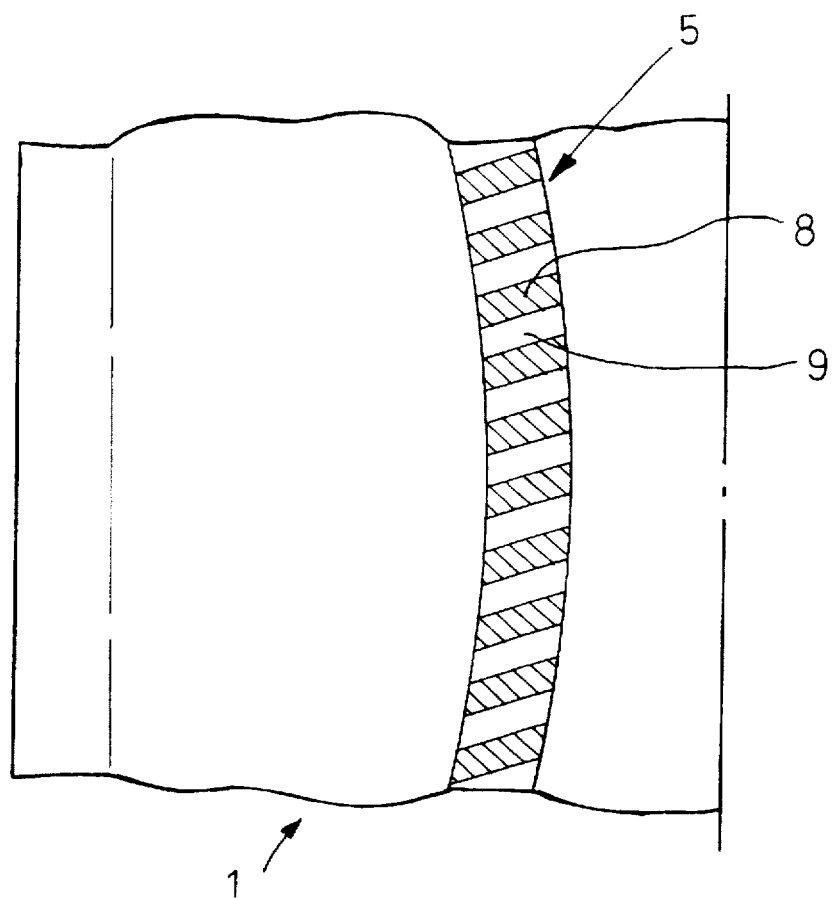
FIG. 2 is a fragmentary plan view showing the sanitary napkin in enlarged scale.
Figure 3:
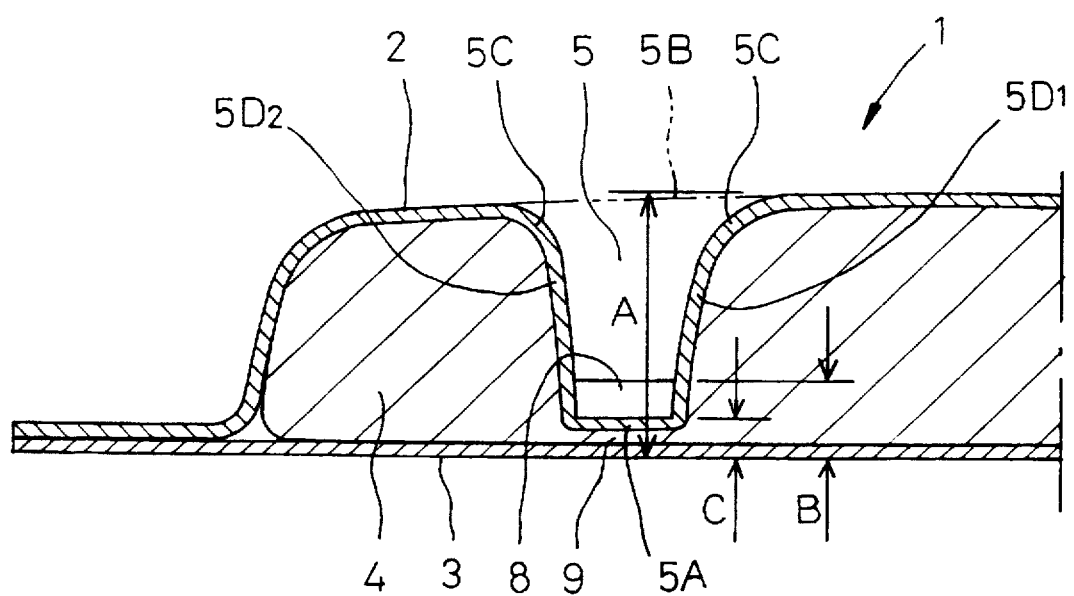
FIG. 3 is a sectional view taken along a line III—III in FIG. 1.

FIG. 2 is a plan view showing a fragment of FIG. 1 in enlarged scale and FIG. 3 is a sectional view taken along line III—III in FIG. 1. As depicted in FIG. 3. a bottom 5A of each groove 5 includes a plurality of lower density compressed zones 8 each having a thickness (height) B and a plurality of higher density compressed zones 9 each having a thickness (height) C. The zones 8. 9 alternate longitudinally of the groove 5. The groove 5 has an upper opening 5B of a width larger than that of the bottom 5A. and upper opening edges 5C describing circular arcs. Both the lower density compressed zones 8 and the higher density compressed zones 9 extend transversely across the bottom 5A. more specifically. obliquely of a longitudinal axis x of the napkin 1 (as seen in FIGS. 1 and 2). The respective zones 8. 9 thus transversely extending across the bottom 5A are narrower than the bottom 5A. The groove 5 is compression-molded so that a dimensional relationship of B=0.7 to 0.2. A. C=0.5; to 0.05; A and B>C. where A represents a thickness of the napkin 1 at the non-compressed region. Preferably the higher density compressed zone 9 is of a density of 0.1 g/cm$^3$ or higher while the lower density compressed zone 8 is of a density lower than that in the higher density compressed zone 9. Preferably. the groove 5 has a length corresponding to ½ to ⅘ of the full length of the core 4 and a width of 1 to 5 mm. Both the lower density compressed zone 8 and the higher density compressed zone 9 preferably have a width of 0.8 to 4 mm as measured longitudinally of the groove 5.

It will be understood that the portions of the core 4 extending respectively along and adjacent to inner and outer side walls $5D_1$. $5D_2$ defining the groove 5 are also more or less influenced by compression-molding of the groove 5 and. as a result. have a density lower than the densities of the compressed zones 8. 9 but higher than the density of the remainder region which was not subjected to any compressive force at all. Referring to FIG. 3. a portion of an upper opening edge 5C continuous with the inner side wall $5D_1$ describes a circular arc which is more gentle. i.e.. longer than. a circular arc described by a portion of another upper opening edge 5C continuous with the outer side wall $5D_2$. Therefore the portion of the core 4 lying under the former is compressed over a larger extend and at a higher density compared to the portion of the core 4 lying under the latter. Accordingly. a quantity of body exudates flowing into the groove 5 tends to be predominantly absorbed by this groove 5 and to spread thereinto on the inner side wall $5D_1$. so the quantity of body exudates will not spread through the outer side wall $5D_2$ toward outer side edges of the napkin causing undesirable sideway leakage. As will be readily understood from such effect, the groove 5 is compression-molded preferably so that the portion of the core 4 lying on the inner side wall $5D_1$ presents a density higher than in the portion of the core 4 lying on the outer side wall $5D_2$.

Such configuration of the groove 5 can be obtained by compressing the napkin 1 in an appropriate mold under a high pressure and can be stabilized by, for example, immersing the region of the napkin 1 to be compressed with a small quantity of water or disposing hot melt adhesive between the topsheet 2 and the core 4 followed by compression under heating.

With the napkin 1 constructed as described above, body exudates rapidly spreads from the lower density compressed zones 9 as soon as body exudates are discharged and flow into the grooves 5 in directions as indicated by arrows P, Q in FIG. 1. Surroundings of the zones 9, on the other hand, are of relatively lower density, so the quantity of body exudates once having been absorbed by the zones 9 hardly spreads into the surroundings. In this manner, the inventive napkin 1 allows body exudates once having flowed into the grooves 5 to be prevented not only from rapidly spreading longitudinally thereof but also from spreading outward toward the transversely opposite side edges of the napkin 1.

To implement the invention, the core 4 may be made of fluff pulp mixed with superabsorptive polymer powder and/ or thermoplastic synthetic fiber. Assuming that the groove 5 is compression-molded under heating, the thermoplastic synthetic fiber can serve to stabilize the resultant configuration of the groove 5. Preferably, the topsheet 2 is made of nonwoven fabric or perforated plastic film and the backsheet 3 is made of plastic film. Bonding of the respective components to form the napkin 1 may be achieved by using suitable adhesive agent, e.g., of hot melt type or so-called heat-sealing technique so far as the components to be bonded together are of heat-sealable nature. It should be noted that no specific means of bonding is illustrated.

The inventive sanitary napkin has a pair of grooves formed on the top surface thereof so as to extend respectively along the transversely opposite sides thereof and these grooves not only provide enhanced fit of the napkin against the wearer's body but also prevent a twist from occurring in the middle region of the napkin and prevent the twist from reaching the peripheral region of the napkin. On the bottom of each groove, there are arranged the relatively high density compressed zones and the relatively low density compressed zones alternately in the longitudinal direction of the bottom. The alternating compressed zones serve to suppress a phenomenon that the quantity of body exudates once having flowed into the grooves might too rapidly spread longitudinally of the grooves and thereby to prevent the transversely opposite side edges of the napkin as well as the wearer's undergarments contacted by these side edges from being stained with any quantity of body exudates.

The groove is formed by compression-molding but presents the upper opening edge describing a circular arc in cross-section making the wearer's body free from uncomfortable stimulus and allows body exudates to flow smoothly into the groove.

The napkin of such type is generally folded at a right angle to the longitudinal direction thereof for individually packaging, resulting in generation of many fine transverse wrinkles in the proximity of the fold. The fine transverse wrinkles may cause sideway leakage of body exudates. However, it has been found that the invention can alleviate generation of fine transverse wrinkles compared to the case in which there are provided neither the grooves nor their bottoms comprising the higher and lower density compressed zones arranged alternately in the longitudinal direction of the grooves, depending on factors such as the particular material of the topsheet.

The portion of the core lying along the inner side wall coextensive with the outer side wall to define each of the grooves has a density higher than in the portion of the core lying along the outer side wall, so body exudates are predominantly absorbed by and spread into the portion of the core lying along the inner side wall and thus sideway leakage of body exudates are effectively avoided.

What is claimed is:

1. An absorbent article comprising;

a liquid-permeable topsheet;

a liquid impermeable backsheet;

a liquid-absorbent core disposed therebetween, said core defining an absorbing region; and said absorbent article having a pair of compression-molded grooves formed in said topsheet and said core, said grooves extending longitudinally along transversely opposite sides of said absorbing region, and said grooves are spaced apart from each other by a distance gradually increasing from the minimum at a longitudinally middle point thereof to the maximum at longitudinally opposite ends thereof, said grooves having higher and lower density compressed zones alternately arranged in a longitudinal direction thereof.

2. A sanitary napkin according to claim 1, wherein said groove has a width at an upper opening thereof larger than a width at a bottom thereof and an edge of said upper opening describes a circular arc in a transverse cross-section.

3. A sanitary napkin according to claim 1, wherein said higher and lower density compressed zones extend obliquely to a longitudinal axis of said napkin.

4. A sanitary napkin according to claim 1, wherein said lower density compressed zone has a vertical dimension larger than the corresponding dimension of said higher density compressed zone as measured from said bottom.

5. A sanitary napkin according to claim 1, wherein said groove is defined by inner and outer side walls and a portion of said core lying along said inner side wall has a density higher than a density in a portion of said core lying along said outer side wall.

\* \* \* \* \*